(12) United States Patent  (10) Patent No.: US 8,399,077 B1
Bekele  (45) Date of Patent: Mar. 19, 2013

(54) POLYGLYCOLIC ACID-BASED FILM (75) Inventor: Solomon Bekele, Taylors, SC (US)

(73) Assignee: Cryovac, Inc., Duncan, SC (US)

( * ) Notice: Subject to any disclaimer, the term of this patent is extended or adjusted under 35 U.S.C. 154(b) by 3 days.

(21) Appl. No.: 13/301,170

(22) Filed: Nov. 21, 2011

(51) Int. Cl.
*B29D 22/00* (2006.01)

(52) U.S. Cl. ............... 428/35.2; 428/35.4; 428/35.7

(58) Field of Classification Search .......... 428/35.2, 428/35.4, 35.7, 212; 383/113; 525/64, 190
See application file for complete search history.

(56) References Cited

U.S. PATENT DOCUMENTS

| | | |
|---|---|---|
| 4,640,865 A | 2/1987 | Lancaster et al. |
| 4,766,035 A | 8/1988 | Lancaster et al. |
| 4,847,155 A | 7/1989 | Lancaster et al. |
| 5,391,423 A * | 2/1995 | Wnuk et al. ............ 428/217 |
| 5,407,713 A | 4/1995 | Wilfong et al. |
| 5,468,526 A | 11/1995 | Allen et al. |
| 5,567,489 A | 10/1996 | Allen et al. |
| 5,643,375 A | 7/1997 | Wilfong et al. |
| 5,895,694 A | 4/1999 | Zavadsky et al. |
| 5,908,917 A | 6/1999 | Kawakami et al. |
| 6,046,251 A | 4/2000 | Kawakami et al. |
| 6,143,383 A | 11/2000 | Giori |
| 6,258,423 B1 | 7/2001 | Giori |
| 6,455,161 B1 | 9/2002 | Regnier et al. |
| 6,620,474 B1 | 9/2003 | Regnier et al. |
| 6,649,888 B2 | 11/2003 | Ryan et al. |
| 7,179,868 B2 | 2/2007 | Yamane et al. |
| 7,270,860 B2 | 9/2007 | Giori |
| 7,517,339 B2 | 4/2009 | Pedersen et al. |
| 7,785,682 B2 | 8/2010 | Sato et al. |
| 2011/0229701 A1* | 9/2011 | Rivett et al. ............ 428/212 |
| 2011/0229722 A1* | 9/2011 | Rivett et al. ............ 428/412 |

* cited by examiner

*Primary Examiner* — N. Edwards
(74) *Attorney, Agent, or Firm* — Alston & Bird LLP (57) ABSTRACT

A film is provided, and in particular, a film having at least one gas barrier layer that comprises a noise-dampening polymer resin and of a polyglycolic acid resin. The polyglycolic-based films provide excellent gas barrier properties while maintaining a desirable level of softness and low noise making them ideal for a variety of medical applications.

24 Claims, 6 Drawing Sheets

POLYGLYCOLIC ACID-BASED FILM

FIELD OF THE INVENTION

The present invention relates generally to films for the production of pouches and in particular gas barrier films that can be used in the production of medical packaging.

BACKGROUND OF THE INVENTION

Multilayer films having gas and odor barrier properties are well known and widely used in food and medical packaging applications. Generally, it is desirable for such films to have good impact resistance, flexibility, barrier properties, and desirable optical properties.

Where the films are to be used in medical applications, such as ostomy applications, they must also possess a unique combination of odor and moisture barrier properties as well as low noise, softness, heat or radio-frequency sealability, skin compatibility, and comfort. Such films have been provided in the past through the use of multi-ply film laminates where at least one of the plies is oxygen and moisture vapor impermeable.

In addition to barrier properties, it is often desirable that polymeric films for use in ostomy applications to not emit noise during use, such as when the film is crumpled or bent, so that the presence of the ostomy pouch is concealed from others. In particular, it has been found that the use of ostomy pouches makes the patient feel uneasy about such containers emitting, especially as the patient moves around, noise of a low but still audible intensity level. Most polymeric films, especially multilayer polymer films comprised of individual polymeric film layers having different rigidities (i.e., modulus), emit noise when crumpled. Such noise may alert others to the presence of the ostomy pouch, which can result in embarrassment to the wearer.

Typically, films currently in use for ostomy applications utilize polyvinylidene chloride (PVDC) or copolymers of vinylidene chloride with a comonomer such as methylacrylate or vinylchloride as the gas barrier layer of a multilayer film. These films usually provide good resistance to odor transmission and are also relatively quiet; however, they are also believed to be hazardous to the environment when disposed of by incineration, a common practice in numerous countries.

Unfortunately, previous efforts to provide films formed of chlorine-free barrier resins have tended to be stiffer and noisier than films utilizing conventional PVDC-based resins and do not match the quality of conventional chlorinated films for use in ostomy appliances. Chlorine-free barrier films aimed at providing a suitably soft multilayer film such that the crumpling or bending of the film during use does not emit noise have resulted, undesirably, in the reduction of gas barrier properties.

Accordingly, there still remains a need for polymeric films, particularly being free from chlorine, having both gas and odor barrier properties while also having a softness level such that the amount of noise emitted during use is mitigated.

BRIEF SUMMARY OF THE INVENTION

In one aspect, the present invention is directed to a multilayer film that exhibits gas and odor barrier properties, and in particular to a film having at least one gas barrier layer comprising a blend of a noise-dampening polymer resin and from about 40 to 80 weight percent of a polyglycolic acid resin. Films according to embodiments of the invention can have an oxygen transmission rate of less than 60 cc/m$^2$·day·atm at 73° F. and at 100% relative humidity and a storage modulus of less than about 2.5×E+09 dynes/cm$^2$ at 40° C. In particular, films in accordance with the present invention have desirable gas/odor barrier properties as well as desirable softness (e.g., storage modulus) at temperature ranges that are within the body temperature range of the person using a pouch formed from multilayer films in accordance with embodiments of the present invention. Preferably, multilayer films according to the present invention are also devoid of chlorine. As a result, films in accordance with the present invention beneficially provide excellent gas/odor barrier properties and mitigated noise emission levels at normal body temperatures. Such films, therefore, are particularly suited for medical applications, such as in ostomy pouches. Exemplary medical applications for films according to embodiments of the present invention include the packaging of medical solutions, containment of human drainage, such as ostomy, colostomy, urostomy pouches, and the like.

In certain embodiments, the multilayer includes first and second exterior layers and at least one gas barrier layer. The gas barrier layer (e.g., barrier for fecal odors) being disposed between the first and second exterior layers. Preferably, the gas barrier layer(s) are disposed between water barrier layers such that water (e.g., moisture vapors) is prevented from contacting the gas barrier layer. In certain embodiments, the external layers provide water barrier properties such that the internal gas barrier layer(s) are shielded from water (e.g., water vapors).

Gas barrier layers in accordance with embodiments of the invention generally include a blend of a noise-dampening polymer resin and from about 40 to 80 weight percent of a polyglycolic acid resin. In certain preferred embodiments, the noise-dampening polymer resin comprises acid anhydride grafted alpha-olefins. Exemplary noise-dampening polymer resins include modified ethylene vinyl acetate, such as ethylene vinyl acetate grafted with maleic anhydride, or a modified ethylene acrylate copolymer, such as maleic anhydride grafted ethylene acrylate copolymer.

Films in accordance with the present invention provide desirable gas barrier properties, and noise reduction (e.g., softness as measured by storage modulus). Accordingly, films in accordance with embodiments of the present invention are particularly useful in medical pouch applications, such as ostomy bags and the like.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

Embodiments of the invention are directed to a composition and films having a combination of both gas/odor barrier properties and noise-dampening properties desirable for use in pouches for a variety of medical applications. Exemplary medical applications for films according to embodiments of the present invention include the packaging of medical solutions, containment of human drainage, such as ostomy, colostomy, urostomy pouches, and the like.

In particular, embodiments of the present invention provide a multilayer film having at least one layer having a combination of gas barrier properties and reduced noisiness. This layer (or layers) having gas barrier properties, also simply referred to as a gas barrier layer, comprises a blend (either a dry blend or a melt blend) of a polyglycolic acid resin and a noise-dampening polymer resin that is capable of reducing the storage modulus of the gas barrier layer, an in particular the polyglycolic acid resin. As discussed in greater detail below, the storage modulus of a film can be used as a good indicator of the noisiness of the film. That is, the tendency of the film to generate noise when it is moved, crumpled, shifted, or the like. In the present invention, the inventor has discovered that a polyglycolic acid resin blended with such a noise-dampening resin can be used to prepare films having good gas barrier properties and low noise.

Figure 1:
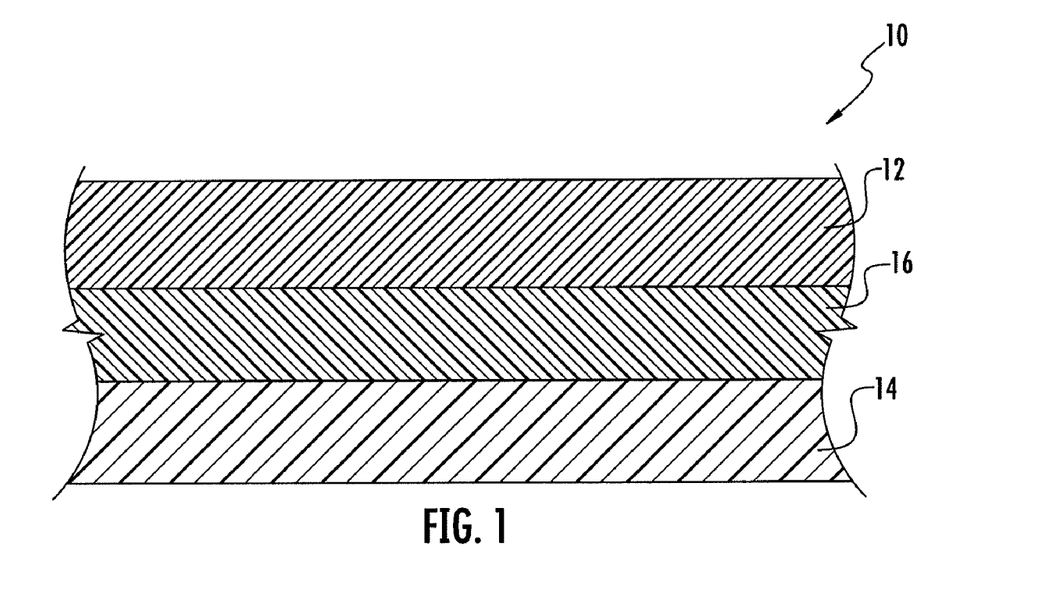
FIG. 1 is a schematic cross-section of a three-layer film in accordance with the present invention.

In one embodiment as shown in FIG. 1, a three-layer film 10 is provide in which the film 10 includes a first exterior layer 12, a second exterior layer 14, and an interior layer 16 positioned between exterior layers 12 and 14. It should be noted, however, that additional layers, e.g., adhesive layers or additional function layers, such as various barrier layers, may be included in film 10 as desired.

In the embodiment illustrated in FIG. 1, at least one of the layers comprises a gas barrier layer comprising a blend of polyglycolic acid resin and a noise-dampening polymer material. Preferably, interior layer 16 comprises a gas barrier layer including a blend of a polyglycolic acid resin and a noise-dampening polymer material. In some embodiments, exterior layers 12 and 14 may each comprise a water barrier layer. In such embodiments, the gas barrier layer is protected from external sources of water, such as moisture vapor, that may cause the gas barrier layer to hydrolyze. In certain embodiments, the water barrier layer can include, but necessarily limited to, heterogeneous ethylene/alpha-olefins including linear low density polyethylene (LLDPE), linear medium density polyethylene (LMDPE), very low density polyethylene (VLDPE), ultra-low density polyethylene (UL-DPE), ethylene-propylene copolymers, and combinations thereof. LLDPE is generally understood to include that group of heterogeneous ethylene/alpha-olefin copolymers which fall into the density range of about 0.915 to about 0.94 g/cc.). In additional embodiments, the exterior layers may comprise an exterior abuse layer or exterior sealant layer of the film, such as a heat or radio frequency (RF) sealable layer.

The polyglycolic acid (PGA) resin in the gas barrier layer can be selected from a wide variety of PGA resins. The PGA resin can include a homopolymer of glycolic acid (including a ring-opening polymerization product of glycolide (GL) that is a bimolecular cyclic ester of glycolic acid) consisting only of glycolic acid-recurring unit represented by formula:

$$\mathrm{-(O-CH_2-CO)_n-} \quad (I)$$

and also a polyglycolic acid copolymer comprising at least 55 wt. % of the above-mentioned glycolic acid-recurring unit.

Examples of comonomer providing the polyglycolic acid copolymer together with a glycolic acid monomer, such as the above-mentioned glycolide, may include: cyclic monomers, such as ethylene oxalate (i.e., 1,4-dioxane-2,3-dione), lactides, lactones (e.g., β-propiolactone, β-butyrolactone, β-pivalolactone, γ-butyrolactone, δ-valerolactone, β-methyl-δ-valerolactone, and ∈-caprolactone), carbonates (e.g., trimethylene carbonate), ethers (e.g., 1,3-dioxane), ether esters (e.g., dioxanone), amides (s-caprolactam); hydroxycarboxylic acids, such as lactic acid, 3-hydroxypropanoic acid, 3-hydroxybutanoic acid, 4-hydroxybutanoic acid and 6-hydroxycaproic acid, and alkyl esters thereof; substantially equi-molar mixtures of aliphatic diols, such as ethylene glycol and 1,4-butanediol, with aliphatic dicarboxylic acids, such as succinic acid and adipic acid, or alkyl esters thereof; and combinations of two or more species of the above.

The content of the above glycolic acid recurring unit in the PGA resin is at least 55 wt. %, preferably at least 70 wt. %, more preferably at least 90 wt. %. If the content is too small, it becomes difficult to attain a gas barrier property-improving effect associated with the PGA resin. Within this extent, the PGA resin may comprise 2 or more species of polyglycolic acid (co-)polymers.

The PGA resin may preferably have a weight-average molecular weight (based on polymethyl methacrylate) in a range of 50,000-800,000, and in particular from about 100,000 to 250,000 or about 150,000 to 250,000, according to GPC measurement using hexafluoroisopropanol solvent. The molecular weight distribution ($M_w/M_n$), also known as "polydispersity," may be determined by gel permeation chromatography. In certain embodiments, the polydispersity ($M_w/M_n$) of PGA can generally range from about 1 to 5, or from about 1.5 to 2.5. A few examples of suitable PGA resins include Kuredux 100R60 (homopolymer), 100E35 (homopolymer), 100T60 (homopolymer), available from Kureha.

In one embodiment, the amount of PGA resin in the gas barrier layer may range from about 20 to 80 (e.g., 40 to 80, 40 to 70, 50-65, 55-65) weight percent, based on the total weight % of the gas barrier layer. In one particular embodiment, the amount of PGA resin in the gas barrier layer is typically from about 40 to 70 weight percent, and more particularly, from about 55 to 65 weight percent.

The noise-dampening polymer resin in the gas barrier layer can be selected from a wide variety of materials that are capable of reducing the storage modulus of the gas barrier layer. As discussed previously, the present invention provides a multilayer film having desirable gas barrier properties while also providing a level of softness or flexibility (as measured by the film's storage modulus) to mitigate noise emitted upon bending or folding of the film. A film's storage modulus can be used to quantify a particular film's ability to be folded or crumpled during use without the emission of a noticeable level of noise. The storage modulus for a film can be readily obtained from Dynamic Mechanical Analysis (DMA). DMA is a technique that can be used to investigate the stiffness or flexibility of a material. Generally speaking, a vibration (e.g., as a sign wave of constant or variable frequency) is imposed on the sample and the modulus of the material can be measured. The storage modulus of a material (e.g., a film) is related to the material's complex Young's modulus:

$$E^* = E' + iE'',$$

where E' represents the storage modulus and E" represents the loss modulus. As such, the detected modulus is split into two quantities, the storage modulus (E') and the loss modulus (E"). The storage modulus is a measure of the energy stored during a cycle, and the loss modulus is a measure of the energy lost. That is, the storage modulus is related to stiffness, and the loss modulus to dampening and energy dissipation. Films according to embodiments of the present invention can beneficially have a relatively low storage modulus such that the film can be easily folded, rolled, and crumpled. This ease in handling, translates into low level emission (e.g., barely detectable if at all) of noise upon use, for example, in medical pouches (e.g., ostomy bags).

Examples of noise-dampening polymer resins that may be blended with the PGA resin can include ethylene vinyl acetate and ethylene acrylates. In certain embodiments, the noise-dampening polymer resin comprises anhydride grafted alpha-olefins. Exemplary noise-dampening polymer resins include modified ethylene vinyl acetate, such as ethylene vinyl acetate grafted with maleic anhydride, or a modified ethylene acrylate copolymer, such as maleic anhydride grafted ethylene acrylate copolymer. In certain embodiments the noise-damping polymer resin can comprise alpha-olefins grafted with other anhydrides besides maleic anhydride. For example, the alpha-olefins can be also be grafted with phthalic anhydride, acetic anhydride, etc. In certain embodiments, the alpha-olefins can be grafted with a combination of various acid anhydrides (e.g., maleic anhydride, phthalic anhydride, acetic anhydride, etc.). Typically, the amount of noise-dampening polymer resin in the gas barrier layer is from about 10 to 60 weight percent based on the total weight of the gas barrier layer, and in particular, from about 20 to 50 weight percent, with about 25 to 45 weight percent, being somewhat more typical. In one embodiment, the gas barrier layer may consist solely of a blend of the PGA resin and the noise-dampening polymer resin. However, in some other embodiments, the gas barrier layer may include additional components to the PGA resin and the noise-dampening polymer resin.

In one embodiment, the noise-dampening polymer resin comprises ethylene vinyl acetate. The term "EVA" or "ethylene vinyl acetate copolymer" refers generally to a copolymer formed with ethylene and vinyl acetate monomers in which the ethylene derived units in the copolymer are present in major amounts, preferably from about 60 to 98% by weight, and the vinyl acetate-derived units in the copolymer are present in minor amounts, preferably from about 2 to 40 percent by weight of the total. In this embodiment, the EVA may have a high vinyl acetate content, for example, from about 5 to 35% (e.g., 8-35%, 5-30%, 10-25, 10-20%%), with a content of about 10 to 28% being somewhat more preferred.

In a preferred embodiment, the EVA is a modified EVA that has been grafted with maleic anhydride functional moieties. In one embodiment, the amount of maleic anhydride in the modified EVA is between 0.1 to 10 weight percent (e.g., 0.1-5.0 weight percent), and in particular, from about 1.0 weight percent or less (e.g., 0.1 to 1.0 weight percent). An example of a modified EVA resin that may be used in the gas barrier layer is Plexar 1007, available from LyondellBassell Industries, and having a vinyl acetate content of 10%.

In one embodiment, the noise-dampening polymer resin may comprise an ethylene acrylate. Suitable ethylene acrylate copolymers for use in the gas barrier layer may include ethylene butyl acrylate (EBA), and ethylene methyl acrylate (EMA). Other suitable may include ethylene-co-n-butyl acrylate-co-carbon monoxide available from DuPont under the tradename Elvaloy HP771™, ethylene-co-n-vinyl acetate-co-carbon monoxide available from DuPont under the tradename Elvaloy HP4924™, and ethylene-co-n-butyl acrylate-co-glycidyl methacrylate available from DuPont under the tradename Elvaloy PTW™. In one embodiment, an anhydride-modified ethylene/methyl acrylate copolymer can be used. Suitable anhydride-modified ethylene/methyl acrylate copolymers are commercially available from DuPont under the tradenames BYNEL™ 21E810 and BYNEL™ 2174. Other anhydride-modified polymers may also be used. In one embodiment, the noise-dampening polymer comprises an ethylene acrylate copolymer modified grafted with a maleic anhydride functional moiety. An example of such a modified ethylene acrylate copolymer is Bynel CXA 21E787 available from DuPont, which is an ethylene methyl acrylate grafted with maleic anhydride.

Figure 2:
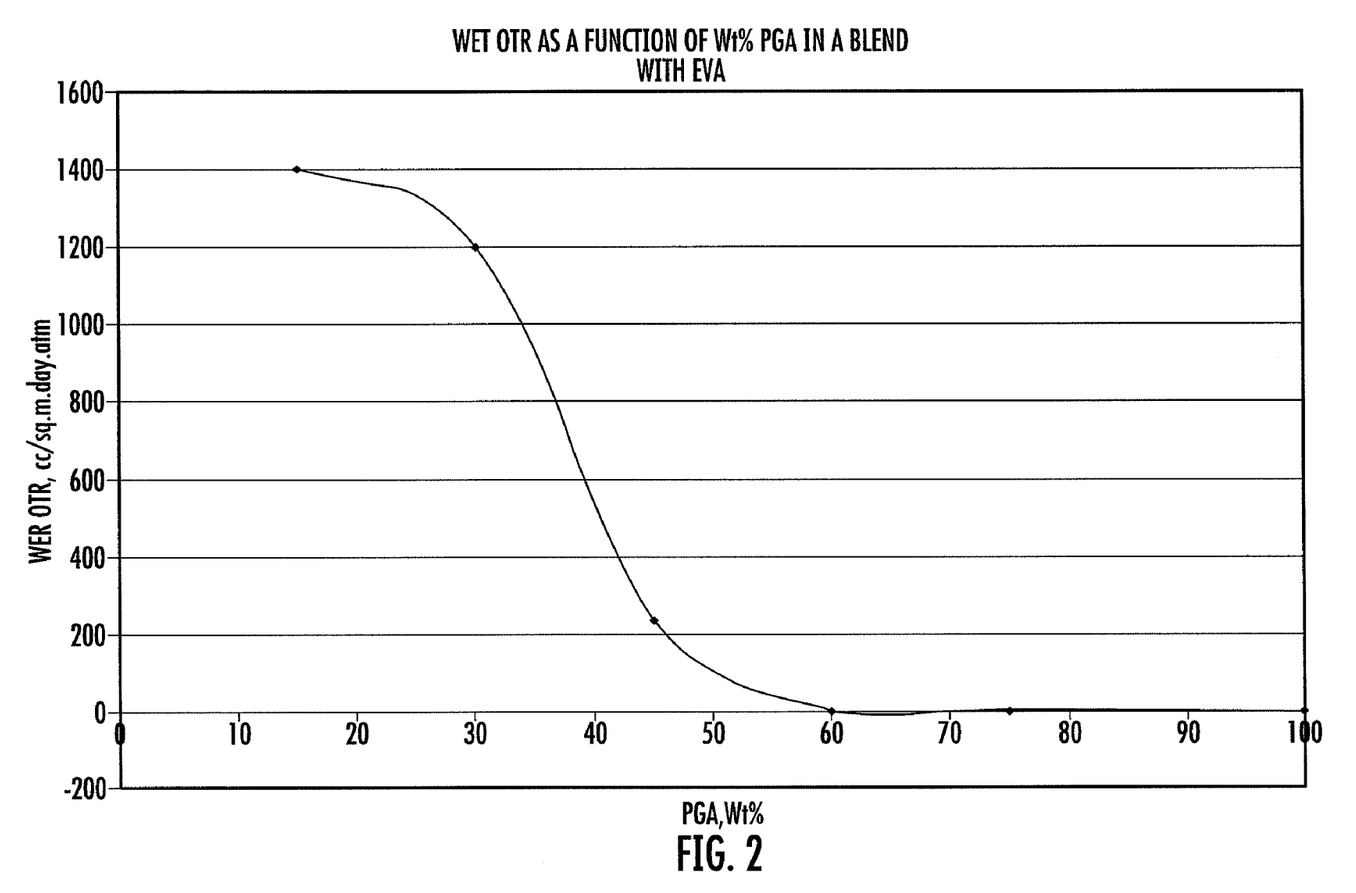
FIG. 2 is a graph showing the oxygen transmission rate for the films described in Table 6 (below)

As noted previously, films in accordance with the invention also have good gas barrier properties. In this regard, FIG. 2 illustrates the oxygen transmission rates at 73° F. and at 100% relative humidity for films having a gas barrier layer comprising a blend of a PGA resin and a modified EVA resin (i.e., data for the films shown in Table 6 below). As illustrated by FIG. 2 the oxygen transmission rate of the blends decreases or improves with an increased percentage of PGA with a sharp decrease in oxygen transmission starting at around a 30 weight percent of PGA content in the blend. In preferred embodiments, the gas barrier layer includes at least about 35% or 40% (e.g., 35-70% or 40-70%) by weight of a PGA blended with a noise-dampening polymer resin as discussed above.

As noted previously, multilayer films according to certain embodiment of the present invention can exhibit a variety of properties rendering them particularly suitable for medical packaging and pouch applications, including ostomy pouches. More specifically, multilayer films according to the present invention can have an oxygen transmission rate of less than 60 (e.g., 1-60, 10-60, 30-60), 50 (e.g., 1-50, 10-50, 25-50), 40 (e.g., 1-40, 10-40, 20-40), or 30 (1-30, 10-30, 1-20, 1-15) cc/m2·day·atm at 73° F. and at 100% relative humidity while also maintaining a commercially viable storage modulus at temperature ranges that are within the body temperature range of the person using a pouch formed from multilayer films in accordance with embodiments of the present invention. For example, the films according to embodiments of the present invention can have a storage modulus of less than about 2.5E+09 (e.g., 1-2.5 E+09, 1-2.0 E+09, or 1.3-2.3 E+09) dynes/cm² at 40° C. as determined by ASTM D-5026 (Sep. 1, 2006)

In embodiments of the present invention, the multilayer film can include one or more gas barrier layers (e.g., 1, 2, 3, 4, or 5 gas barrier layers) comprising a blend of a PGA resin and a noise-dampening polymer resin. It has been found that films having at least one gas barrier layer comprising a blend of a PGA resin and a noise-dampening polymer resin, preferably from 40-70 wt. percent of PGA resin based on the weight of the gas barrier layer, have desirable high gas barrier properties and low noise performance in medical applications (e.g., ostomy pouches). During normal use of ostomy pouches, the temperature to which the pouch is exposed is typically greater than that of the ambient room temperature. This increase is typically a result of the temperature of the fluids within the pouch or the proximity of the pouch to the wearer. Films in accordance with the present invention provide excellent gas barrier properties and reductions in emitted noise levels at a slightly elevated temperature range (e.g., 30-40° C. or 35-40° C.) and are particularly suited for medical applications, such as in ostomy pouches.

In a further embodiment, the film 10 of FIG. 1 may also include RF sealable properties. An RF sealable film may be particularly useful in the construction of ostomy pouches. In such an embodiment, the exterior surfaces of the film are RF sealable to each other or itself.

In one embodiment, an RF sealable film is provided in which one or more of the exterior layers comprise an RF sealable material comprising a blend of and an ethylene/alpha-olefin copolymer and an of ethylene vinyl acetate (EVA) or an ethylene acrylate copolymer, or a combination of a EVA or ethylene acrylate copolymer. The inventors of the present invention have discovered that by blending an ethylene/alpha olefin with an EVA and/or ethylene acrylate copolymer, wherein the amount of the ethylene acrylate copolymer is from about 20 to 80 weight percent of the blend, RF sealable films with peel strengths in excess of 500 g/inch can be obtained. The amount of EVA or ethylene acrylate copolymer in the exterior layer is typically from about 50 to 70 weight %, based on the total weight of the film, and more typically at least about 50 weight %. In certain embodiments, polyurethane-based components can also be incorporated into the RF sealable films.

As in the gas barrier layer discussed above, suitable ethylene acrylate copolymers for use in an RF sealable exterior layer may include ethylene butyl acrylate (EBA), and ethylene methyl acrylate (EMA). Other suitable may include ethylene-co-n-butyl acrylate-co-carbon monoxide available from DuPont under the tradename Elvaloy HP771™, ethylene-co-n-vinyl acetate-co-carbon monoxide available from DuPont under the tradename Elvaloy HP4924™, and ethylene-co-n-butyl acrylate-co-glycidyl methacrylate available from DuPont under the tradename Elvaloy PTW™. In embodiments comprising EMA or EBA, the amount of ethylene acrylate copolymer is generally at least about 35 weight percent. Suitable ethylene/alpha-olefin copolymers for use in the present invention are discussed in greater detail below.

In a further embodiment of the invention, the exterior layers comprise a blend of a blend of an ethylene acrylate copolymer, such as those discussed above, an ethylene/alpha-olefin copolymer, and a styrene-vinyl polyisoprene-styrene block-co-polyisopyrene block triblock polymer ("SVPSPI"). In this embodiment, the content of the ethylene acrylate copolymer typically ranges from 20 to 80 weight percent of each layer In RF sealable film applications, the film has a dielectric loss factor of at least 0.02 and is capable of being radio frequency sealed. Unless stated to the contrary, the dielectric loss factor was determined in accordance with ASTM D 150 (Aug. 1, 2011). Films in accordance with the invention provide RF seals having peel strengths on the order of 500 g/in or greater as measure in accordance with ASTM F 88 (Jun. 15, 2009). In some embodiments, the peel strength of the RF seals are greater than 1000 g/in., and in particular, greater than about 2,000 g/in.

When the multilayer film of the present invention is used to form a pouch (e.g., single or multi-compartment pouches), such as an I.V. bag, ostomy pouch, or air-bladder portion of a compression device, the first exterior layer preferably forms the outer surface of the pouch (i.e., the surface which is exposed to the environment) while the second exterior layer forms the inner surface of the pouch (i.e., the surface which is in contact with the inside of the pouch and, therefore, with the product, drainage, or air which is enclosed within the pouch). In this fashion, the first exterior layer can provide the pouch with puncture or abuse-resistance, and gloss, as well as a high degree of flexibility and strength as noted above. The second exterior layer can serve as a sealant layer. In this role, peripheral portions of the second exterior layer are joined, e.g., by radio frequency (RF) sealing, to form an enclosure for containing or collection of a fluid therein. In addition to RF sealing, embodiments of the invention can also be sealed with heat sealing, ultrasound sealing, and the like. The pouch preferably includes one or more inlets for introducing components that are to be confined within the pouch. In one embodiment, the pouch comprises a container having a flexible bag-like shape. The shape and size of the pouch may be varied depending upon its intended use and need.

Figure 3:
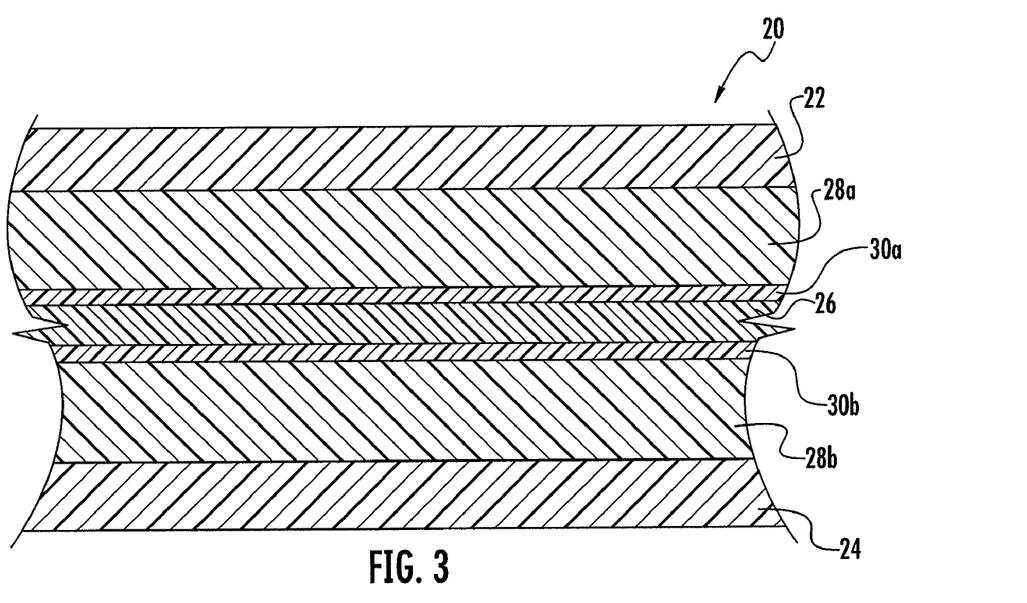
FIG. 3 is a schematic cross-section of a multilayer film in accordance with the present invention.

FIG. 3 illustrates another embodiment of the invention in which a seven-layer film 20 is provided that is also particularly useful in ostomy pouch applications in which two of the layers of the film comprise gas/odor barrier layers 30a, 30b including a polyglycolic acid resin. In one particular embodiment, the present invention provides an RF sealable film in which exterior layers 22, 24 comprise a blend of an ethylene/alpha-olefin copolymer and an ethylene acrylate copolymer. Interior layer 26 may be a functional or core layer as discussed above. In certain embodiments, interior layer 26 acts as a softening layer to facilitate an increased level of flexibility. It should be noted, however, that such an internal layer 26 is optional. Interior layers 28a and 28b are disposed between the outer exterior layers 22, 24 and interior layer 26. Gas/odor barrier layers 30a, 30b are each disposed between interior layers 28a, 28b and interior layer 26. In a preferred embodiment, the corresponding layers disposed on opposite sides of interior layer 26 are the same or similar to each other. For example, layers 22 and 24 are preferably the same or of a similar composition as is also the case with layers 28a and 28b. Interior layer 26 may comprise a wide variety of materials including an ethylene/alpha olefin, ethylene acrylate copolymer, or a combination thereof.

In the illustrated embodiment, the interior layers 28a and 28b are the bulk layers of the film and help to provide strength and integrity to the film. In one embodiment, interior layers 28a and 28b also contribute to the RF sealability of the film. In one such embodiment, interior layers 28a and 28b and each exterior layer comprise a blend of an ethylene/alpha-olefin copolymer and an ethylene vinyl acetate or ethylene acrylate copolymer. In one particular embodiment, the exterior layers may comprise from about 40 to 80 weight percent of an ethylene vinyl acetate or ethylene acrylate copolymer, and from about 20 to 50 weight percent of an ethylene/alpha-olefin, and the interior layers 28a and 28b may each independently comprise a blend of LLDPE and EVA in which the EVA is present in an amount from about 20 to 80 weight percent and the LLDPE is present in an amount from about 20 to 80 weight percent. The interior layers 28a and 28b may also each comprise a blend of LLDPE and EVA, in which the EVA is present in an amount of at least 50 weight percent and the LLDPE is present in an amount from about 35 to 50 weight percent.

External layers 22, 24 and/or internal bulk layers 28a, 28b can also function as water barrier layers. In this fashion, the gas barrier layers 30a, 30b are protected from external sources of water, such as moisture vapor, that may cause the gas barrier layers to hydrolyze.

A wide variety of ethylene/alpha-olefin (EAO) copolymers may be used in the practice of the present invention. The term "ethylene/alpha-olefin copolymer" generally designates copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches. These polymers are obtained by low pressure polymerization processes and the side branching which is present will be short compared to non-linear polyethylenes (e.g., LDPE, a polyethylene homopolymer). The polyethylene polymers may be either heterogeneous or homogeneous.

Heterogeneous ethylene/alpha-olefin copolymers are ethylene/alpha-olefin copolymerization reaction products of relatively wide variation in molecular weight and composition distribution, and which are prepared using conventional Ziegler-Natta or other heterogeneous catalysts. Examples of heterogeneous ethylene/alpha-olefins include linear low density polyethylene (LLDPE), linear medium density polyethylene (LMDPE), very low density polyethylene (VLDPE), and ultra-low density polyethylene (ULDPE). LLDPE is generally understood to include that group of heterogeneous ethylene/alpha-olefin copolymers which fall into the density range of about 0.915 to about 0.94 g/cc. Sometimes linear polyethylene in the density range from about 0.926 to about 0.94 is referred to as LMDPE. Lower density heterogeneous ethylene/alpha-olefin copolymers are VLDPE (typically used to refer to the ethylene/butene copolymers available from Union Carbide with a density ranging from about 0.88 to about 0.91 g/cc) and ULDPE (typically used to refer to the ethylene/octene copolymers supplied by Dow). EAOs are copolymers of ethylene and one or more alpha-olefins, the copolymer having ethylene as the majority mole-percentage content. In some embodiments, the comonomer includes one or more $C_3$-$C_{20}$ alpha-olefins, such as one or more $C_4$-$C_{12}$ alpha-olefins, or one or more $C_4$-$C_8$ alpha-olefins. Particularly useful alpha-olefins include 1-butene, 1-hexene, 1-octene, and mixtures thereof.

Useful EAOs include those having a density of less than about any of the following: 0.925, 0.922, 0.92, 0.917, 0.915, 0.912, 0.91, 0.907, 0.905, 0.903, 0.9, and 0.86 grams/cubic centimeter (g/cm$^3$). Unless otherwise indicated, all densities herein are measured according to ASTM D1505 (Jul. 1, 2010). In one embodiment, the EAO has a density from about 0.84 to 0.91 g/cm$^3$.

As is known in the art, heterogeneous polymers have a relatively wide variation in molecular weight and composition distribution. Heterogeneous polymers may be prepared with, for example, conventional Ziegler Natta catalysts.

On the other hand, homogeneous polymers are typically prepared using metallocene or other single site-type catalysts. Such single-site catalysts typically have only one type of catalytic site, which is believed to be the basis for the homogeneity of the polymers resulting from the polymerization. Homogeneous polymers are structurally different from heterogeneous polymers in that homogeneous polymers exhibit a relatively even sequencing of comonomers within a chain, a mirroring of sequence distribution in all chains, and a similarity of length of all chains. As a result, homogeneous polymers have relatively narrow molecular weight and composition distributions. Examples of homogeneous polymers include the metallocene-catalyzed linear homogeneous ethylene/alpha-olefin copolymer resins available from the Exxon Chemical Company (Baytown, Tex.) under the EXACT trademark, linear homogeneous ethylene/alpha-olefin copolymer resins available from the Mitsui Petrochemical Corporation under the TAFMER trademark, and long-chain branched, metallocene-catalyzed homogeneous ethylene/alpha-olefin copolymer resins available from the Dow Chemical Company under the AFFINITY trademark.

More particularly, homogeneous ethylene/alpha-olefin copolymers may be characterized by one or more properties known to those of skill in the art, such as molecular weight distribution ($M_w/M_n$), composition distribution breadth index (CDBI), narrow melting point range, and single melt point behavior. The molecular weight distribution ($M_w/M_n$), also known as "polydispersity," may be determined by gel permeation chromatography. Homogeneous ethylene/alpha-olefin copolymers which can be used in the present invention generally have an $M_w/M_n$, of less than 2.7; such as from about 1.9 to 2.5; or from about 1.9 to 2.3 (in contrast heterogeneous ethylene/alpha-olefin copolymers generally have a $M_w/M_n$ of at least 3). The composition distribution breadth index (CDBI) of such homogeneous ethylene/alpha-olefin copolymers will generally be greater than about 70 percent. The CDBI is defined as the weight percent of the copolymer molecules having a comonomer content within 50 percent (i.e., plus or minus 50%) of the median total molar comonomer content. The CDBI of linear ethylene homopolymer is defined to be 100%. The Composition Distribution Breadth Index (CDBI) is determined via the technique of Temperature Rising Elution Fractionation (TREF). CDBI determination may be used to distinguish homogeneous copolymers (i.e., narrow composition distribution as assessed by CDBI values generally above 70%) from VLDPEs available commercially which generally have a broad composition distribution as assessed by CDBI values generally less than 55%. TREF data and calculations therefrom for determination of CDBI of a copolymer may be calculated from data obtained from techniques known in the art, such as, for example, temperature rising elution fractionation as described, for example, in Wild et. al., J. Poly. Sci. Poly. Phys. Ed., Vol. 20, p. 441 (1982). In some embodiments, homogeneous ethylene/alpha-olefin copolymers have a CDBI greater than about 70%, i.e., a CDBI of from about 70% to 99%. In general, homogeneous ethylene/alpha-olefin copolymers useful in the present invention also exhibit a relatively narrow melting point range, in comparison with "heterogeneous copolymers", i.e., polymers having a CDBI of less than 55%. In some embodiments, the homogeneous ethylene/alpha-olefin copolymers exhibit an essentially singular melting point characteristic, with a peak melting point ($T_m$), as determined by Differential Scanning calorimetry (DSC), of from about 60° C. to 105° C. In one embodiment, the homogeneous copolymer has a DSC peak $T_m$ of from about 80° C. to 100° C. As used herein, the phrase "essentially single melting point" means that at least about 80%, by weight, of the material corresponds to a single $T_m$ peak at a temperature within the range of from about 60° C. to 105° C., and essentially no substantial fraction of the material has a peak melting point in excess of about 115° C., as determined by DSC analysis. DSC measurements are made on a Perkin Elmer SYSTEM 7™ Thermal Analysis System. Melting information reported are second melting data, i.e., the sample is heated at a programmed rate of 10° C./min. to a temperature below its critical range. The sample is then reheated (2nd melting) at a programmed rate of 10° C./min.

A homogeneous ethylene/alpha-olefin copolymer can, in general, be prepared by the copolymerization of ethylene and any one or more alpha-olefin. For example, the alpha-olefin is a $C_3$-$C_{20}$ alpha-monoolefin, such as a $C_4$-$C_{12}$ or a $C_4$-$C_8$ alpha-monoolefin. For example, the alpha-olefin comprises at least one member selected from the group consisting of butene-1, hexene-1, and octene-1, i.e., 1-butene, 1-hexene, and 1-octene, respectively, or a blend of hexene-1 and butene-1.

Processes for preparing and using homogeneous polymers are disclosed in U.S. Pat. No. 5,206,075, to HODGSON, Jr., U.S. Pat. No. 5,241,031, to MEHTA, and PCT International Application WO 93/03093, each of which is hereby incorporated herein by reference thereto, in its entirety. Further details regarding the production and use of homogeneous ethylene/alpha-olefin copolymers are disclosed in PCT International Publication Number WO 90/03414, and PCT International Publication Number WO 93/03093, both of which designate Exxon Chemical Patents, Inc. as the Applicant, and both of which are hereby incorporated herein by reference thereto, in their respective entireties.

Still another species of homogeneous ethylene/alpha-olefin copolymers is disclosed in U.S. Pat. No. 5,272,236, to LAI, et al., and U.S. Pat. No. 5,278,272, to LAI, et al., both of which are hereby incorporated herein by reference thereto, in their respective entireties.

In one particular embodiment, the ethylene/alpha-olefin copolymer comprises a linear low density polyethylene (LLDPE) composed of copolymers of ethylene and comonomers of 1-butene. Desirably, the content of butene is from about 8 to 16 weight %. An exemplary commercially available LLDPE that can be used in accordance with the present invention is Sabic® 518N or Sabic 118N available from Saudi Basic Industries Corporation.

Although not illustrated in FIGS. 2 and 3, films according to certain embodiment of the present invention can also include adhesive or tie layers. Adhesive layers may include any suitable adhesive material, such as, e.g., anhydride-modified EVA copolymer, anhydride-modified EMA copolymer, and anhydride-modified EBA copolymer, unmodified EVA, unmodified EMA and unmodified EnBA with comonomer content of about 6 to 30 weight %.

Of the foregoing materials, anhydride-modified EVA copolymer is preferred, particularly those in which the vinyl acetate content thereof is 25 weight percent or more. A preferred such material is "BYNEL CXA E-361" from DuPont.

Adhesive layers may comprise a material selected from the group consisting of anhydride-modified EVA copolymer; anhydride-modified ethylene/acrylate copolymer (e.g., anhydride-modified EMA copolymer, anhydride-modified ethylene/ethyl acrylate copolymer, and anhydride-modified EBA copolymer); anhydride-modified ethylene/alpha-olefin (EAO) copolymer (e.g., anhydride-modified linear low density polyethylene and anhydride-modified very low density polyethylene); homogeneous ethylene/alpha-olefin copolymer, particularly those having a density of less than about 0.89 g/cc (e.g., ethylene/octene copolymer); anhydride-modified high density polyethylene; and mixtures of the foregoing materials.

Suitable anhydride-modified EMA copolymers are commercially available from DuPont under the tradename BYNEL™, and from LyondellBassell Industries under the tradename PLEXAR™. Anhydride-modified linear low density polyethylene is commercially available from Mitsui under the tradename ADMER™, and from DuPont under the tradename BYNEL™. Each of the other materials which can be used for adhesive layers 24 and 28 are also commercially available.

The total thickness of film 20 may range from about 25 to about 150 microns, with a range from about 50 to 100 microns being preferred. When present, interior layers 28a and 28b typically each comprise from about 20 to 40% of the thickness of the film, and in particular, from about 25 to 35% of the film's thickness, with about 30% of the film's thickness being somewhat more typical. Interior layers 28a, 28b of the film generally have a thickness from about 15 to 45 microns, and in particular, from about 20 to 30 microns. Exterior layers 22, 24 are typically, but not always, of a thinner gauge than bulk interior layers 28a, 28b. In one embodiment, the exterior layers 22, 24 of the film may be from about 3 to 30 microns, with a thickness of 3 to 10 being preferred.

The gas barrier layers 30a, 30b can each range from about 1 to 50% (e.g., 3 to 20%) of the film's thickness, and in particular, from about 3 to 10% of the film's thickness. Layers 30a, 30b of the film generally have a thickness from about 3 to 15 microns, and in particular, from about 3 to 10 microns. As discussed previously, certain embodiments of the present invention include only a single gas barrier layer. In such embodiments, the single gas barrier layer can range from about 1 to 50% (e.g., 3 to 20%) of the film's thickness, and in particular, from about 3 to 10% of the film's thickness. The single gas barrier layer of the film generally can have a thickness from about 3 to 15 microns, and in particular, from about 3 to 10 microns.

The interior layer 26 can generally have a thickness that is from about 3 to 15 microns, with a thickness of about 5 to 10 being preferred. In the event that adhesive layers are incorporated into the film, their thickness generally ranges from about 3 to 10 microns, and in particular from about 3 to 5 microns in thickness. It should be recognized that the overall thickness of the film and the thickness of individual layers is not limited to any specific range provided the desired properties and processability of the film is maintained.

As can be appreciated by those having ordinary skill in this art, the multilayer films of the present invention are not limited to the three or seven-layer structures described above. Films having fewer or greater numbers of layers, e.g., two, four, six, seven, eight, nine, or more, are included within the scope of the present invention. For example, additional high density polyethylene layer(s) may be included in the film in order to increase the moisture barrier capabilities of the film if such an increase is desired. Additional oxygen barrier layer(s) may also be included if desired.

Various additives can be used in any or all of the layers of the multilayer films of the present invention. Such additives include, without limitation, antiblocking agents, antioxidants, processing aids such as calcium stearate, pigments, antistatic agents, odor absorbers, odor scavengers, etc. Where the multilayer film is to be used to for making medical solution pouches, the amount of additive included in the film is preferably kept to a minimum in order to minimize the likelihood that such additives will be extracted into the medical solution.

The multilayer films of the present invention can be formed by cast coextrusion or blown coextrusion as a tubular film. Containers for medical applications or other end uses can be made directly from the coextruded, tubular film, or alternatively from rollstock material obtained from the tube after it has been slit and ply-separated. A hot blown process can also be used to make the film. Other processes, such as extrusion coating, conventional lamination, slot die extrusion, etc., can also be used to make the multilayer film of the present invention, although these alternative processes can be more difficult or less efficient than the above methods.

Multilayer films in accordance with the invention may have low haze characteristics. Haze is a measurement of the transmitted light scattered more than 2.5° from the axis of the incident light. Haze is measured according to the method of ASTM D1746 (Feb. 1, 2009), which is incorporated herein in its entirety by reference. All references to "haze" values in this application are by this standard. In some embodiments, the haze of either multilayer film is no more than about 20%, 15%, 10%, 9%, 8%, 7%, 6%, 5%, 4%, and 3%.

The film may have a gloss (i.e., specular gloss) as measured against the outside layer—measured at a time selected from before the forming step or after the forming step—of at least about any of the following values: 40%, 50%, 60%, 63%, 65%, 70%, 75%, 80%, 85%, 90%, and 95%. These percentages represent the ratio of light reflected from the sample to the original amount of light striking the sample at the designated angle. All references to "gloss" values in this application are in accordance with ASTM D 2457 (45° angle) (2010), which is incorporated herein in its entirety by reference.

The film may be transparent (at least in any non-printed or non-pigmented regions) so that a packaged article may be visible through the film. "Transparent" means that the film transmits incident light with negligible scattering and little absorption, enabling objects (e.g., the packaged article or print) to be seen clearly through the film under typical viewing conditions (i.e., the expected use conditions of the material). The regular transmittance (i.e., clarity) of the film—measured at a time selected from before the forming step or after the forming step—may be at least about any of the following values: 65%, 70%, 75%, 80%, 85%, and 90%, measured in accordance with ASTM D1003 (Apr. 15, 2011). All references to "regular transmittance" values in this application are by this standard.

The total luminous transmittance (i.e., total transmittance) of the film—measured at a time selected from before the forming step or after the forming step—may be at least about any of the following values: 65%, 70%, 75%, 80%, 85%, and 90%, measured in accordance with ASTM D1003. All references to "total luminous transmittance" values in this application are by this standard.

The measurement of optical properties of plastic films, including the measurement of total transmission, haze, clarity, and gloss, is discussed in detail in Pike, LeRoy, "Optical Properties of Packaging Materials," Journal of Plastic Film & Sheeting, vol. 9, no. 3, pp. 173-80 (July 1993), of which pages 173-80 is incorporated herein by reference.

The multilayer films of the present invention have been described in connection with medical applications. However, it is to be understood that other applications for the films are also possible, and that this disclosure should not be construed as being limited only to medical pouches or devices.

The invention may be further understood by reference to the following examples, which are provided for the purpose of representation, and are not to be construed as limiting the scope of the invention.

EXAMPLES

The films produced in the Examples were prepared by a cast process. The materials used in the films are identified below. All percentages are weight percents unless indicated otherwise. All physical property and compositional values are approximate unless indicated otherwise.

"EVA-1": Elvax 3170SB; 18% VA EVA with slip and antiblock from Dupont.

"EVA-2": Elvax 3170; 18% VA EVA from Dupont.

"EVA-3": Plexar 1007, 10% VA EVA grafted with maleic anhydride from LyondellBassell Industries.

"VLPDE-1": Affinity 8100G; Metallocene VLPDE with octane copolymer, density of 0.867 from Dow Chemical.

LPDE-1 (this material is used as an edge encapsulation and is not part of the film):

LDPE, PE1042cs15 from Flint Hills.

"PGA-1": Kuredux 100R600, polyglycolic acid from Kureha.

"LPDE-2": Ampacet 10850; slip and antiblock masterbatch in LDPE from Ampacet.

"ABS-1": CC101393562F, an odor absorber masterbatch consisting of MgO, ZnO, and Zeolite from PolyOne Corp.

"EAC-1": Bynel CXA 21E787; maleic anhydride grafted ethylene acrylate copolymer from DuPont.

In the following Examples Sets, several multilayer films have been prepared and their respective storage modulus and OTR have been obtained as a function of temperature. Films according to embodiments of the present invention, as shown in the Example Sets, provide excellent gas barrier properties and softness/quietness as indicated by their storage modulus (particularly in temperature ranges commensurate with use of ostomy pouches).

Example Set 1

Table 1, provided below, shows the construction of nine (9) different multilayer films incorporating two gas barrier layers comprising a blend of a polyglycolic acid resin and anethylene vinyl acetate. In particular, layers 4 and 6 comprise gas barrier layers.

TABLE 1

Nine (9) Layer Films

| | | A | B | C | D | E | F | G | H | I | |
|---|---|---|---|---|---|---|---|---|---|---|---|
| | Extruder | 2.5 | 4.0 | 2.5 | 4.5 | 3.0 | 4.5 | 2.5 | 4.0 | 3.0 | J |
| | Layer | 1 | 2 | 3 | 4 | 5 | 6 | 7 | 8 | 9 | Encapsulation |
| Film 1-1A | | EVA-1 | EVA-2 [70%] VLPDE-1 [30%] | EVA-3 [80%] VLPDE-1 [20%] | PGA-1 [55%] EVA-3 [45%] | EVA-3 [80%] VLPDE-1 [20%] | PGA-1 [55%] EVA-3 [45%] | EVA-3 [80%] VLPDE-1 [20%] | EVA-2 [70%] VLPDE-1 [30%] | EVA-1 | LPDE-1 |
| Mils | | 0.15 | 0.90 | 0.15 | 0.15 | 0.30 | 0.15 | 0.15 | 0.90 | 0.15 | 75μ |
| Vol% | | 5.0 | 30.0 | 5.0 | 10.0 | 10.0 | | 5.0 | 30.0 | 5.0 | |
| Film 1-1B | | EVA-1 | EVA-2 [70%] VLPDE-1 [30%] | EVA-3 [80%] VLPDE-1 [20%] | PGA-1 [55%] EVA-3 [45%] | EVA-3 [80%] VLPDE-1 [20%] | PGA-1 [55%] EVA-3 [45%] | EVA-3 [80%] VLPDE-1 [20%] | EVA-2 [70%] VLPDE-I [30%] | EVA-1 | LPDE- I |
| Mils | | 0.15 | 0.83 | 0.15 | 0.23 | 0.30 | 0.22 | 0.15 | 0.83 | 0.15 | 75μ |
| Vol% | | 5.0 | 27.5 | 5.0 | 15.0 | 10.0 | | 5.0 | 27.5 | 5.0 | |
| Film 1-2A | | EVA-1 | EVA-2 [70%] VLPDE-1 [30%] | EVA-3 [80%] VLPDE-1 [20%] | PGA-1 [60%] EVA-3 [40%] | EVA-3 [80%] VLPDE-1 [20%] | PGA-1 [60%] EVA-3 [40%] | EVA-3 [80%] VLPDE-1 [20%] | EVA-2 [70%] VLPDE-1 [30%] | EVA-1 | LPDE-1 |
| Mils | | 0.15 | 0.90 | 0.15 | 0.15 | 0.30 | 0.15 | 0.15 | 0.90 | 0.15 | 75μ |
| Vol% | | 5.0 | 30.0 | 5.0 | 10.0 | 10.0 | | 5.0 | 30.0 | 5.0 | |

TABLE 1-continued

Nine (9) Layer Films

|  | | A | B | C | D | E | F | G | H | I | |
|---|---|---|---|---|---|---|---|---|---|---|---|
|  | Extruder | 2.5 | 4.0 | 2.5 | 4.5 | 3.0 | 4.5 | 2.5 | 4.0 | 3.0 | J |
|  | Layer | 1 | 2 | 3 | 4 | 5 | 6 | 7 | 8 | 9 | Encapsulation |
| Film 1-2B | | EVA-1 | EVA-2 [70%] VLPDE-1 [30%] | EVA-3 [80%] VLPDE-1 [20%] | PGA-1 [60%] EVA-3 [40%] | EVA-3 [80%] VLPDE-1 [20%] | PGA-1 [60%] EVA-3 [40%] | EVA-3 [80%] VLPDE-1 [20%] | EVA-2 [70%] VLPDE-1 [30%] | EVA-1 | LPDE-1 |
| Mils | | 0.15 | 0.83 | 0.15 | 0.23 | 0.30 | 0.22 | 0.15 | 0.83 | 0.15 | 75μ |
| Vol% | | 5.0 | 27.5 | 5.0 | 15.0 | 10.0 | | 5.0 | 27.5 | 5.0 | |
| Film 1-3A | | EVA-1 | EVA-2 [70%] VLPDE-1 [30%] | EVA-3 [80%] VLPDE-1 [20%] | PGA-1 [70%] EVA-3 [30%] | EVA-3 [80%] VLPDE-1 [20%] | PGA-1 [70%] EVA-3 [30%] | EVA-3 [80%] VLPDE-1 [20%] | EVA-2 [70%] VLPDE-I [30%] | EVA-1 | LPDE-1 |
| Mils | | 0.15 | 0.90 | 0.15 | 0.15 | 0.30 | 0.15 | 0.15 | 0.90 | 0.15 | 75μ |
| Vol% | | 5.0 | 30.0 | 5.0 | 10.0 | 10.0 | | 5.0 | 30.0 | 5.0 | |
| Film 1-3B | | EVA-1 | EVA-2 [70%] VLPDE-1 [30%] | EVA-3 [80%] VLPDE-1 [20%] | PGA- I [70%] EVA-3 [30%] | EVA-3 [80%] VLPDE-1 [20%] | PGA-1 [70%] EVA-3 [30%] | EVA-3 [80%] VLPDE-1 [20%] | EVA-2 [70%] VLPDE-1 [30%] | EVA-1 | LPDE-1 |
| Mils | | 0.15 | 0.83 | 0.15 | 0.23 | 0.30 | 0.22 | 0.15 | 0.83 | 0.15 | 75μ |
| Vol% | | 5.0 | 27.5 | 5.0 | 15.0 | 10.0 | | 5.0 | 27.5 | 5.0 | |
| Film 1-4 | | EVA-1 | EVA-2 [70%] VLPDE-1 [30%] | EVA-3 [80%] VLPDE-1 [20%] | PGA-1 [70%] EVA-3 [30%] | EVA-3 [80%] VLPDE-1 [20%] | PGA-1 [70%] EVA-3 [30%] | EVA-3 [80%] VLPDE-1 [20%] | EVA-2 [70%] VLPDE-1 [30%] | EVA-2 [75%] LPDE-2 [05%] ABS-1 [20%] | LPDE-1 |
| Mils | | 0.15 | 0.90 | 0.15 | 0.15 | 0.30 | 0.15 | 0.15 | 0.39 | 0.66 | 75μ |
| Vol% | | 5.0 | 30.0 | 5.0 | 10.0 | 10.0 | | 5.0 | 13.0 | 22.3 | |

Figure 4:
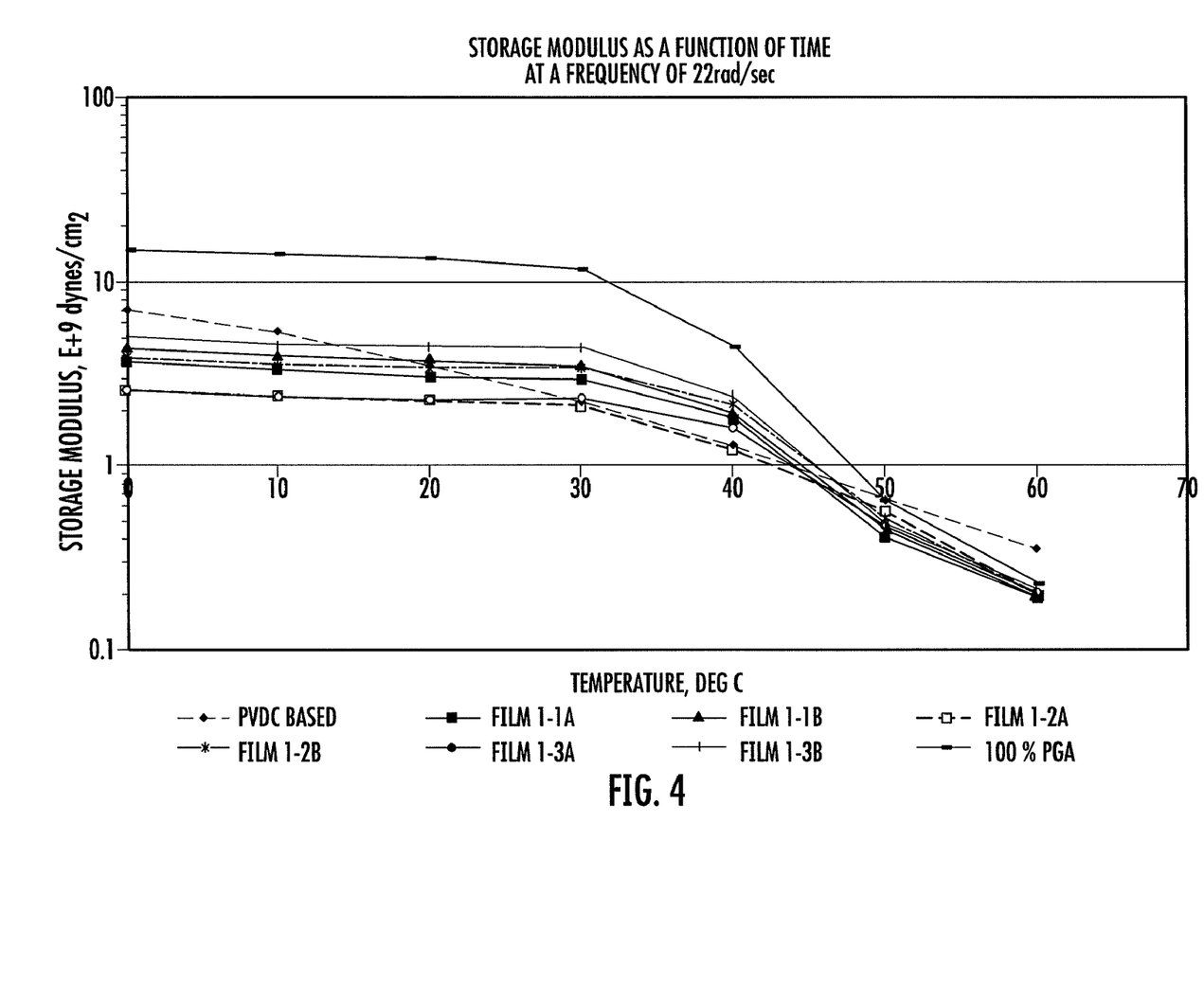
FIG. 4 illustrates the storage modulus for certain multilayer films as a function of temperature.

Table 2, below, provides the storage modulus data for each of the films described in Table 1. FIG. 4 provides a graphical illustration for the data from Table 2.

TABLE 2

Storage Modulus (E+09 dynes/cm$^2$) as function of temperature at a frequency of 22rad

| Temp. °C. | PVDC Based Film* | Film 1-1A | Film 1-1B | Film 1-2A | Film 1-2B | Film 1-3A | Film 1-3B | 100% PGA |
|---|---|---|---|---|---|---|---|---|
| 0 | 7 | 3.7 | 4.4 | 2.6 | 3.94 | 2.61 | 5.06 | 14.8 |
| 10 | 5.4 | 3.338 | 4.01 | 2.42 | 3.6 | 2.42 | 4.6 | 14.1 |
| 20 | 3.6 | 3.16 | 3.78 | 2.26 | 3.5 | 2.34 | 4.51 | 13.6 |
| 30 | 2.3 | 3.04 | 3.56 | 2.2 | 3.5 | 2.38 | 4.54 | 11.9 |
| 40 | 1.34 | 1.89 | 2 | 1.28 | 2.29 | 1.7 | 2.5 | 4.6 |
| 50 | 0.7 | 0.44 | 0.46 | 0.6 | 0.54 | 0.5 | 0.5 | 0.69 |
| 60 | 0.38 | 0.21 | 0.21 | 0.21 | 0.21 | 0.21 | 0.23 | 0.25 |

*NEXCEL MF film (MF513/MF514) available from Sealed Air (USA).

Figure 5:
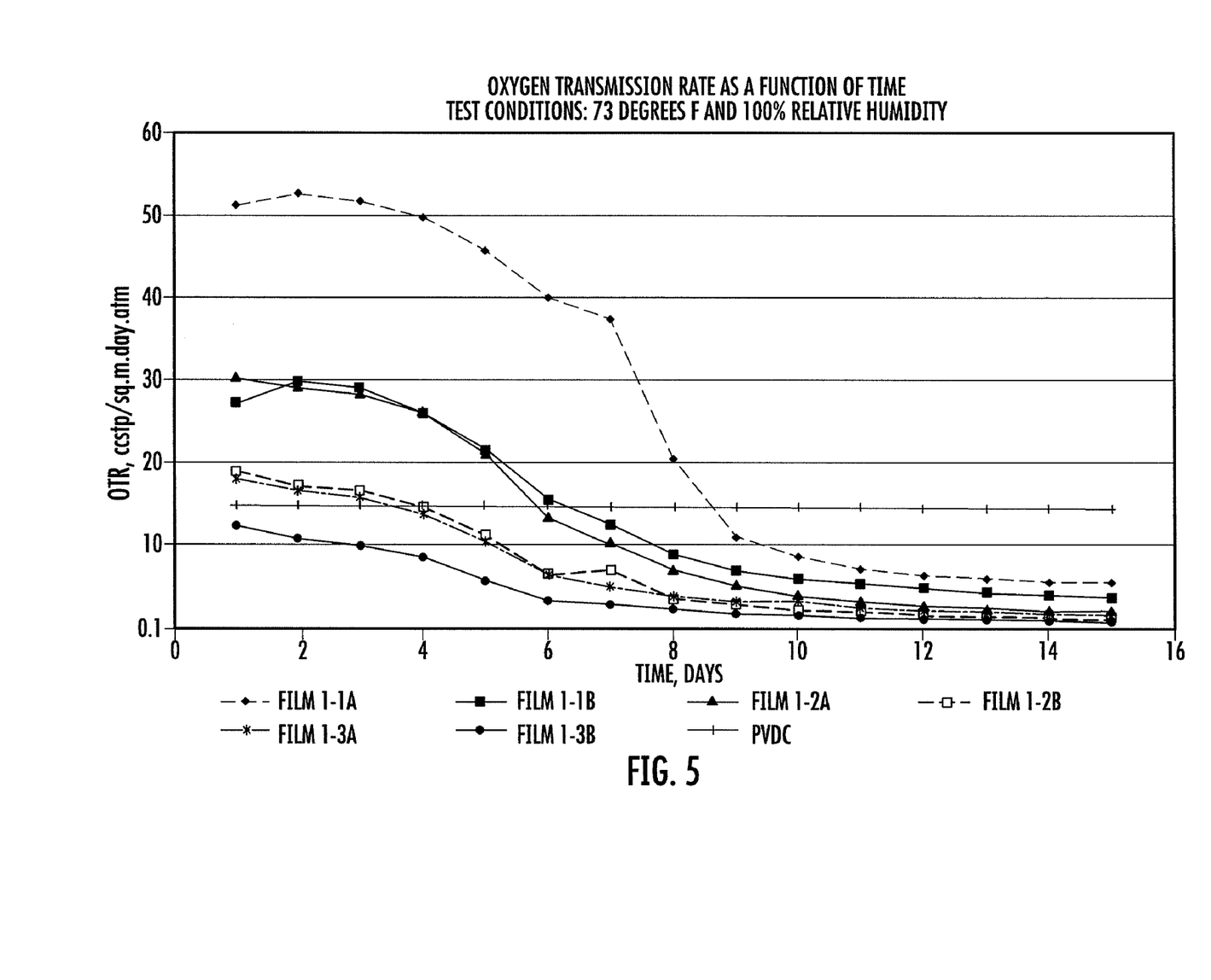
FIG. 5 illustrates the oxygen transmission rate as a function of time for certain multilayer films.

Table 3, below, provides the data obtained upon measuring the gas barrier properties of each of the films described in Table 1 above. FIG. 5 is a graphical illustration of the data in Table 3. The PVDC data are representative of standard films utilizing PVDC as a gas barrier layer.

TABLE 3

Oxygen Transmission Rate as a function of time at 73° F. and 100% relative humidity; ASTM D3985 (2010).

| Days | Film 1-1A | Film 1-1B | Film 1-2A | Film 1-2B | Film 1-3A | Film 1-3B | Standard PVDC Film* |
|---|---|---|---|---|---|---|---|
| 1 | 51.3 | 27.3 | 30.3 | 18.9 | 18.1 | 12.4 | 14.8 |
| 2 | 52.7 | 29.8 | 29.2 | 17.3 | 16.7 | 10.8 | 14.8 |
| 3 | 51.8 | 29.1 | 28.4 | 16.6 | 15.9 | 10 | 14.8 |
| 4 | 49.8 | 26.1 | 26.3 | 14.6 | 14 | 8.7 | 14.8 |
| 5 | 45.8 | 21.7 | 21.2 | 11.3 | 10.7 | 5.8 | 14.8 |
| 6 | 40.1 | 15.7 | 13.6 | 6.7 | 6.6 | 3.4 | 14.8 |
| 7 | 37.5 | 12.7 | 10.7 | 7.2 | 5.2 | 3 | 14.8 |
| 8 | 20.8 | 9.2 | 7.3 | 3.8 | 4.1 | 2.5 | 14.8 |
| 9 | 11.3 | 7.2 | 5.5 | 3.1 | 3.5 | 2 | 14.8 |
| 10 | 8.9 | 6.3 | 4.4 | 2.5 | 3.6 | 1.8 | 14.8 |
| 11 | 7.5 | 5.7 | 3.6 | 2.2 | 2.9 | 1.6 | 14.8 |
| 12 | 6.7 | 5.2 | 3 | 1.8 | 2.5 | 1.4 | 14.8 |

TABLE 3-continued

Oxygen Transmission Rate as a function of time at 73° F.
and 100% relative humidity; ASTM D3985 (2010).

| Days | Film 1-1A | Film 1-1B | Film 1-2A | Film 1-2B | Film 1-3A | Film 1-3B | Standard PVDC Film* |
|---|---|---|---|---|---|---|---|
| 13 | 6.4 | 4.7 | 2.7 | 1.7 | 2.3 | 1.4 | 14.8 |
| 14 | 6 | 4.5 | 2.6 | 1.6 | 2.2 | 1.3 | 14.8 |
| 15 | 6 | 4.2 | 2.6 | 1.4 | 2 | 1.3 | 14.8 |

*NEXCEL MF film (MF513/MF514) available from Sealed Air (USA).

Example Set 2

Table 4, provided below, shows the construction of different multilayer films each having five (5) layers. Each of the films in Table 4 incorporate a single gas barrier layer comprising a blend of a polyglycolic acid resin and an ethylene vinyl acetate. In particular, layer 3 comprises a gas barrier layer. Table 4 also provides the steady state OTR associated with each film. Test conditions for obtaining the OTR values were that same as that in Example Set 1 (e.g., 73° F. and 100% relative humidity). Although not explicitly shown, the OTR values as a function of time for these particular films are similar to days 13-15 in Table 3 above.

TABLE 4

Five (5) Layer Films

| Film # | | Layer 1 | Layer 2 | Layer 3 | Layer 4 | Layer 5 | Steady State OTR, cc/sq.m. day.atm |
|---|---|---|---|---|---|---|---|
| Film 2-1 | | EVA-2 [95%] LPDE-2 [05%] | EVA-3 | EVA-3 [50%] PGA-1 [50%] | EVA-3 | EVA-2 [95%] LPDE-2 [05%] | 18.7 |
| | Vol% | 35.0 | 10.0 | 10.0 | 10.0 | 35.0 | |
| | Mils | 1.05 | 0.30 | 0.30 | 0.30 | 1.05 | |
| Film 2-2 | | EVA-2 [95%] LPDE-2 [05%] | EVA-3 | EVA-3 [50%] PGA-1 [50%] | EVA-3 | EVA-2 [95%] LPDE-2 [05%] | 3.6 |
| | Vol% | 32.5 | 10.0 | 15.0 | 10.0 | 32.5 | |
| | Mils | 1.05 | 0.30 | 0.45 | 0.30 | 1.05 | |
| Film 2-3 | | EVA-2 [95%] LPDE-2 [05%] | EVA-3 | EVA-3 [45.0%] PGA-1 [55.0%] | EVA-3 | EVA-2 [95%] LPDE-2 [05%] | 4.1 |
| | Vol% | 32.5 | 10.0 | 12.5 | 10.0 | 32.5 | |
| | Mils | 1.05 | 0.30 | 0.375 | 0.30 | 1.05 | |
| Film 2-4 | | EVA-2 [95%] LPDE-2 [05%] | EVA-3 | EVA-3 [40%] PGA-1 [60%] | EVA-3 | EVA-2 [95%] LPDE-2 [05%] | 3.4 |
| | Vol% | 35.0 | 10.0 | 10.0 | 10.0 | 35.0 | |
| | Mils | 1.05 | 0.30 | 0.30 | 0.30 | 1.05 | |
| Film 2-5 | | EVA-2 [95%] LPDE-2 [05%] | EVA-3 | EVA-3 [40%] PGA-1 [60%] | EVA-3 | EVA-2 [95%] LPDE-2 [05%] | 2.4 |
| | Vol% | 32.5 | 10.0 | 15.0 | 10.0 | 32.5 | |
| | Mils | 1.05 | 0.30 | 0.45 | 0.30 | 1.05 | |
| Film 2-6 | | EVA-2 [95%] LPDE-2 [05%] | EVA-3 | EAC-1 [50%] PGA-1 [50%] | EVA-3 | EVA-2 [95%] LPDE-2 [05%] | 4.2 |
| | Vol% | 35.0 | 10.0 | 10.0 | 10.0 | 35.0 | |
| | Mils | 1.05 | 0.30 | 0.30 | 0.30 | 1.05 | |
| Film 2-7 | | EVA-2 [95%] LPDE-2 [05%] | EVA-3 | EAC-1 [40%] PGA-1 [60%] | EVA-3 | EVA-2 [95%] LPDE-2 [05%] | 2.3 |
| | Vol% | 32.5 | 10.0 | 15.0 | 10.0 | 32.5 | |
| | Mils | 1.05 | 0.30 | 0.45 | 0.30 | 1.05 | |

Table 5, below, provides the storage modulus data for each of the films described in Table 4.

TABLE 5

Storage Modulus (E+09 dynes/cm$^2$) as function of
temperature at a frequency of 22rad/sec

| Temp ° C. | Film 2-1 | Film 2-2 | Film 2-3 | Film 2-4 | Film 2-5 | Film 2-6 | Film 2-7 |
|---|---|---|---|---|---|---|---|
| 0 | 3.3 | 3.8 | 4 | 3.6 | 4.4 | 2.8 | 8.6 |
| 10 | 2.8 | 3.26 | 3.4 | 3.2 | 4 | 2.4 | 8.2 |
| 20 | 2.58 | 2.9 | 3.3 | 2.84 | 3.8 | 2.23 | 7.9 |
| 30 | 2.3 | 2.45 | 2.7 | 2.5 | 3.2 | 1.9 | 6 |
| 40 | 0.95 | 1.2 | 1.3 | 1.22 | 1.45 | 0.95 | 1.8 |
| 50 | 0.3 | 0.31 | 0.32 | 0.3 | 0.3 | 0.28 | 0.27 |
| 60 | 0.19 | 0.18 | 0.18 | 0.17 | 0.18 | 0.17 | 0.17 |

Example Set 3

Table 6, provided below, shows the construction of six (6) different multilayer films, five (5) of which incorporating a single gas barrier layer comprising a blend of a polyglycolic acid resin and an ethylene vinyl acetate. In particular, layer 3 for films 2-6 in Table 6 comprises a gas barrier layer. The OTR values for these films are illustrated in FIG. 2, which illustrates the impact of the PGA content on the performance of multilayer films.

TABLE 6

Five (5) Layer Films

| Film # | | Layer 1 | Layer 2 | Layer 3 | Layer 4 | Layer 5 |
|---|---|---|---|---|---|---|
| Film 3-1 | | EVA-2 [95%] LPDE-2 [05%] | EVA-3 | EVA-3 | EVA-3 | EVA-2 [95%] LPDE-2 [05%] |
| | Vol% | 32.5 | 10 | 15 | 10 | 32.5 |
| | Mils | 0.975 | 0.30 | 0.45 | 0.30 | 0.975 |
| Film 3-2 | | EVA-2 [95%] LPDE-2 [05%] | EVA-3 | EVA-3 [85%] PGA-1 [15%] | EVA-3 | EVA-2 [95%] LPDE-2 [05%] |
| | Vol% | 32.5 | 10 | 15 | 10 | 32.5 |
| | Mils | 0.975 | 0.30 | 0.45 | 0.30 | 0.975 |
| Film 3-3 | | EVA-2 [95%] LPDE-2 [05%] | EVA-3 | EVA-3 [70%] PGA-1 [30%] | EVA-3 | EVA-2 [95%] LPDE-2 [05%] |
| | Vol% | 32.5 | 10 | 15 | 10 | 32.5 |
| | Mils | 0.975 | 0.30 | 0.45 | 0.30 | 0.975 |

TABLE 6-continued

Five (5) Layer Films

| Film # | | Layer 1 | Layer 2 | Layer 3 | Layer 4 | Layer 5 |
|---|---|---|---|---|---|---|
| Film 3-4 | | EVA-2 [95%] LPDE-2 [05%] | EVA-3 | EVA-3 [55%] PGA-1 [45%] | EVA-3 | EVA-2 [95%] LPDE-2 [05%] |
| | Vol% | 32.5 | 10 | 15 | 10 | 32.5 |
| | Mils | 0.975 | 0.30 | 0.45 | 0.30 | 0.975 |
| Film 3-5 | | EVA-2 [95%] LPDE-2 [05%] | EVA-3 | EVA-3 [40%] PGA-1 [60%] | EVA-3 | EVA-2 [95%] LPDE-2 [05%] |
| | Vol% | 32.5 | 10 | 15 | 10 | 32.5 |
| | Mils | 0.975 | 0.30 | 0.45 | 0.30 | 0.975 |
| Film 3-6 | | EVA-2 [95%] LPDE-2 [05%] | EVA-3 | EVA-3 [25%] PGA-1 [75%] | EVA-3 | EVA-2 [95%] LPDE-2 [05%] |
| | Vol% | 32.5 | 10 | 15 | 10 | 32.5 |
| | Mils | 0.975 | 0.30 | 0.45 | 0.30 | 0.975 |

Figure 6:
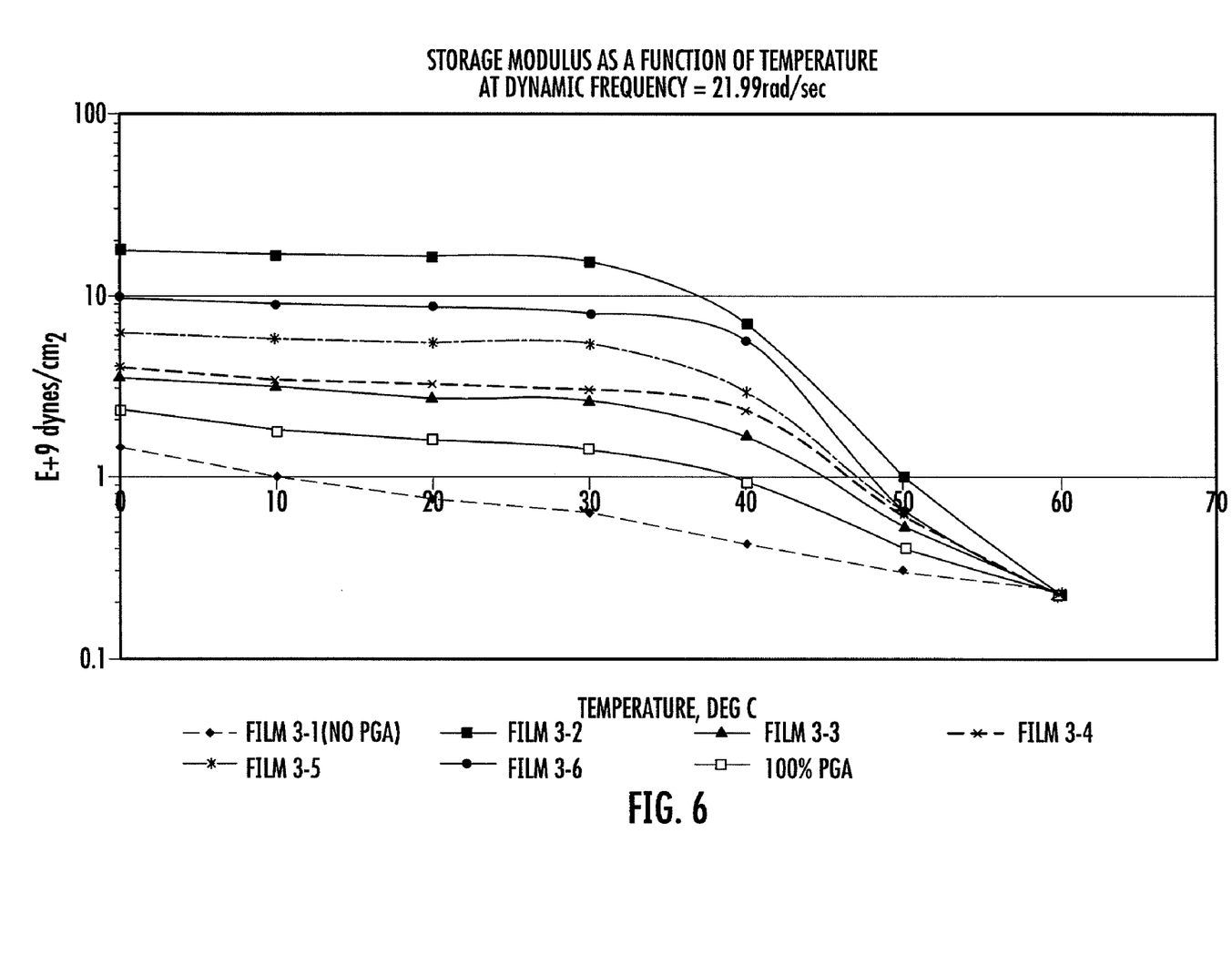
FIG. 6 illustrates the storage modulus for certain multilayer films as a function of temperature.

Table 7, provided below, provides the storage modulus data for each of the films described in Table 6. FIG. 6 provides a graphical illustration of the storage modulus data from Table 7.

TABLE 7

Storage Modulus (E+09 dynes/cm$^2$) as a function of temperature at 22 rad/sec

| Temp °C. | Film 3-1 | Film 3-2 | Film 3-3 | Film 3-4 | Film 3-5 | Film 3-6 | 100% PGA |
|---|---|---|---|---|---|---|---|
| 0 | 1.44 | 2.3 | 3.5 | 4 | 6.2 | 9.9 | 18.2 |
| 10 | 1 | 1.78 | 3.1 | 3.4 | 5.8 | 9.1 | 17.3 |
| 20 | 0.76 | 1.58 | 2.7 | 3.2 | 5.5 | 8.7 | 16.8 |
| 30 | 0.63 | 1.41 | 2.6 | 3 | 5.4 | 8 | 15.4 |
| 40 | 0.43 | 0.94 | 1.65 | 2.3 | 2.9 | 5.6 | 7 |
| 50 | 0.3 | 0.4 | 0.53 | 0.6 | 0.63 | 0.65 | 1 |
| 60 | 0.23 | 0.23 | 0.23 | 0.22 | 0.22 | 0.22 | 0.22 |

Observations and Results

Gas Barrier Properties

As illustrated by the Examples above, films including a gas barrier layer having of at least 35% or 40% by weight polyglycolic acid provide a desirable level of gas barrier properties, particularly for ostomy applications. For instance, such films generally provide similar (and in some cases better) better blockage of gas than traditional PVDC-based films such as NEXCEL MF films (MF513/MF514) available from Sealed Air (USA). Films in accordance with the present invention, therefore, beneficially provide excellent gas/odor barrier properties for ostomy applications without using chlorine-based components and mitigated noise emission levels at normal body temperatures. Such films, therefore, are particularly suited for medical applications, such as in ostomy pouches.

Storage Modulus

Films from the above Examples were also evaluated for storage modulus as a means of quantifying the level of noise emission. The above Examples illustrate that films in accordance with the present invention not only have desirably gas/odor barrier properties, but also exhibit a desirable softness/flexibility (e.g., storage modulus) at temperature ranges that are within the body temperature range of a person using a pouch formed from multilayer films in accordance with embodiments of the present invention. For instance, such films generally provide similar (and in some cases better) better blockage of gas than traditional PVDC-based films (such as NEXCEL MF films (MF513/MF514) available from Sealed Air (USA)) within the temperature ranges (e.g., 35-40° C.) that are within the body temperature range of a person using a pouch formed from multilayer films.

Optical Properties

The optical properties of the films including one or more gas barriers in accordance with embodiments of the present invention were also investigated. As shown in Table 8, provided below, films including a polyglycolic acid-based gas barrier unexpectedly also provided excellent total light transmission and % haze.

TABLE 8

Optical Properties of films from Table 6 (i.e., films 3-1 through 3-6)

| Film | Wt. % of Plexar 1007 | % Haze | % Total Transmission |
|---|---|---|---|
| 100% PGA | 0 | 8.7 | 94.1 |
| Film 3-6 | 25 | 16.8 | 94 |
| Film 3-5 | 40 | 17.5 | 94 |
| Film 3-4 | 55 | 20 | 94 |
| Film 3-3 | 70 | 16.3 | 94.1 |
| Film 3-2 | 85 | 13.8 | 94.1 |
| Film 3-1 | 100 | 12.1 | 93.9 |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A multilayer film, comprising: at least one gas barrier layer comprising a blend of a noise-damping polymer resin and from about 40 to 80 weight percent of a polyglycolic acid resin, said film having an oxygen transmission rate of less than 60 cc/m$^2$*day·atm at 73° F. and at 100% relative humidity.

2. The film of claim 1, wherein the film has a storage modulus of less than about 2.5×E+09 dynes/cm$^2$ at 40° C.

3. The film of claim 1, wherein the film has a storage modulus of between about 1.3-2.3×E+09 dynes/cm$^2$ at 40° C.

4. The film of claim 1, wherein the at least one gas barrier layer is disposed between two exterior layers.

5. The film of claim 1, wherein the noise-damping polymer resin comprise a modified ethylene vinyl acetate (EVA).

6. The film of claim 5, wherein the noise-damping polymer resin comprises EVA grafted with maleic anhydride.

7. The film of claim 6, wherein the EVA includes a vinyl acetate (VA) content from about 5 to 35%.

8. The film of claim 1, wherein the film includes two of said at least one gas barrier layers, and wherein said at least two gas barrier layers are interior layers of the film.

9. The film of claim 1, wherein the film includes two or more water barrier layers positioned relative to the at least one gas barrier layer such that the at least one gas barrier layer is protected from external water sources.

10. The film of claim 1, wherein the film is devoid of chlorine.

11. A film, comprising: two exterior layers and an interior gas barrier layer disposed between the exterior layers, the gas barrier layer comprises from about from about 40 to 80 weight percent of a polyglycolic acid resin and a noise-damping polymer resin.

12. The film of claim 11, wherein the noise-damping polymer resin comprises ethylene vinyl acetate (EVA) having a vinyl acetate (VA) content from 5 to 20%, said EVA being grafted with maleic anhydride.

13. The film of claim 12, wherein the film has a storage modulus of less than about $2.5 \times E+09$ dynes/cm$^2$ at 40° C.

14. The film of claim 12, wherein the film has a storage modulus of between about $1.3$-$2.3 \times E+09$ dynes/cm$^2$ at 40° C.

15. A pouch for the packaging and administration of medical solutions, the pouch being formed from the film of claim 11.

16. A pouch for the collection of human drainage, the pouch being formed from the film of claim 11.

17. A multilayer film, comprising:
first and second water barrier layers;
at least one gas barrier layer disposed between the first and second water barrier layers, said at least one gas barrier comprising a blend of a noise-dampening polymer resin and from about 40 to 80 weight percent of a polyglycolic acid resin,
said film having an oxygen transmission rate of less than 60 cc/m$^2$*day·atm at 73° F. and at 100% relative humidity and a storage modulus of less than about $2.5 \times E+09$ dynes/cm$^2$ at 40° C.

18. The film of claim 17, wherein the first and second water barrier layers or provided as external layers for the film.

19. The film of claim 17, wherein the film has a storage modulus of between about $1.3$-$2.3 \times E+09$ dynes/cm$^2$ at 40° C.

20. The film of claim 17, wherein the film is devoid of chlorine.

21. The film of claim 17, wherein the gas barrier layer comprises from about 55 to 65 weight percent of a polyglycolic acid resin.

22. The film of claim 17, wherein the polyglycolic acid has an average molecular weight from about 50,000 to about 800,000.

23. The film of claim 17, wherein the noise-damping polymer resin comprises a maleic anhydride grafted ethylene acrylate copolymer.

24. A pouch for the collection of human drainage, the pouch being formed from the film of claim 17.

* * * * *

UNITED STATES PATENT AND TRADEMARK OFFICE
CERTIFICATE OF CORRECTION

PATENT NO. : 8,399,077 B1
APPLICATION NO. : 13/301170
DATED : March 19, 2013
INVENTOR(S) : Bekele Page 1 of 1

It is certified that error appears in the above-identified patent and that said Letters Patent is hereby corrected as shown below:

In the Specifications

Column 4,
Line 16, "(s-caprolactam)" should read --(ε-caprolactam)--.

Signed and Sealed this
Ninth Day of July, 2013

Teresa Stanek Rea
*Acting Director of the United States Patent and Trademark Office*